United States Patent [19]

Das

[11] Patent Number: 4,670,453
[45] Date of Patent: Jun. 2, 1987

[54] 7-OXABICYCLOHEPTANE SUBSTITUTED AMIDO-CARBAMOYL PROSTAGLANDIN ANALOGS USEFUL IN THE TREATMENT OF THROMBOTIC DISEASE

[75] Inventor: Jagabandhu Das, Plainsboro, N.J.

[73] Assignee: E. R. Squibb & Sons, Inc., Princeton, N.J.

[21] Appl. No.: 860,973

[22] Filed: May 8, 1986

[51] Int. Cl.$^4$ .................. A61K 31/34; C07D 307/00
[52] U.S. Cl. ........................... 514/382; 514/469; 548/253; 549/463
[58] Field of Search .............. 549/463; 548/253; 514/382, 469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,615 | 6/1984 | Nakane et al. | 424/285 |
| 4,456,617 | 6/1984 | Nakane et al. | 424/285 |

FOREIGN PATENT DOCUMENTS 0043292  8/1982  European Pat. Off. .
0082646  6/1983  European Pat. Off. .
2039909  8/1980  United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted amidocarbamoyl prostaglandin analogs are provided having the structural formula

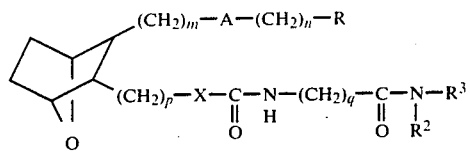

wherein m is 0 to 4; A is —CH=CH— or —CH$_2$—CH$_2$—; n is 1 to 5; $R^1$ is CO$_2$H, CO$_2$alkyl, CO$_2$alkali metal, CO$_2$polyhydroxyamine salt,

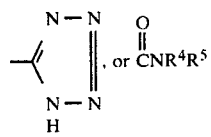

wherein $R^4$ and $R^5$ are the same or different and are H, lower alkyl, hydroxy, lower alkoxy or aryl, at least one of $R^4$ and $R^5$ being other than hydroxy and lower alkoxy; p is 1 to 4; X is O or S; $R^2$ is H or lower alkyl; and $R^3$ is lower alkyl, lower alkenyl, aryl, arylalkyl, cycloalkyl or cycloalkylalkyl.

The compounds are cardiovascular agents useful, for example, in the treatment of thrombotic disease.

16 Claims, No Drawings

7-OXABICYCLOHEPTANE SUBSTITUTED AMIDO-CARBAMOYL PROSTAGLANDIN ANALOGS USEFUL IN THE TREATMENT OF THROMBOTIC DISEASE

DESCRIPTION OF THE INVENTION

The present invention relates to 7-oxabicycloheptane substituted amido-carbamoyl prostaglandin analogs which are cardiovascular agents useful, for example, in the treatment of thrombotic disease. These compounds have the structural formula

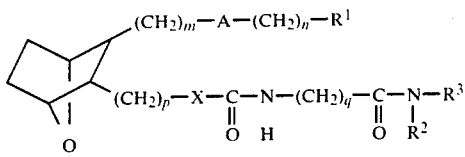

including all stereoisomers thereof, wherein m is 0 to 4; A is $-CH=CH-$ or $-CH_2-CH_2-$; n is 1 to 5; $R^1$ is $CO_2H$, $CO_2$alkyl, $CO_2$ alkali metal, $CO_2$polyhydroxyamine salt,

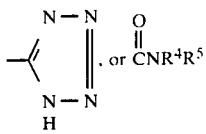

wherein $R^4$ and $R^5$ are the same or different and are H, lower alkyl, hydroxy, lower alkyl or aryl, at least one of $R^4$ and $R^5$ being other than hydroxy and lower alkoxy; p is 1 to 4; X is O or S; q is 1 to 6; $R^2$ is H or lower alkyl; and $R^3$ is lower alkyl, lower alkenyl, aryl, arylalkyl, cycloalkyl or cycloalkylalkyl.

Thus, the compounds of the invention include the following:

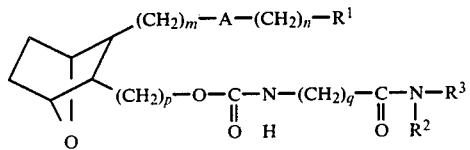

and

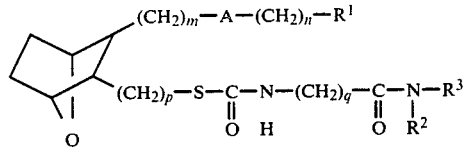

The term "lower alkyl" or "alkyl" as employed herein alone or as part of another group contains 1 to 12 carbons, and preferably 1 to 7 carbons in the normal chain, and includes both straight and branched chain carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkylaryl substituent, a haloaryl substituent, a cycloalkyl substituent, an alkylcycloalkyl substituent, hydroxy, an amino substituent, an amido substituent, an alkylamino substituent, an arylamino substituent, an alkanoylamino substituent, an arylcarbonylamino substituent, a thioamido substituent, a nitro substituent, a cyano substituent, a thiol substituent, an arylthio substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 amino groups, 1 or 2 alkylamino groups, 1 or 2 arylamino groups, 1 or 2 alkanoylamino groups, 1 or 2 arylcarbonylamino groups, 1 or 2 amido groups, 1 or 2 nitro groups, 1 or 2 cyano groups, 1 or 2 thioamido groups, 1 or 2 thiol groups, 1 or 2 arylthio groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like and may be substituted by any of the substituents set out hereinbefore with respect to the definition of the "alkyl" group.

The terms $(CH_2)_m$, $(CH_2)_n$, $(CH_2)_p$ and $(CH_2)_q$ include straight or branched chain radicals having from 0 to 4 carbons in the normal chain in the case of $(CH_2)_m$, from 1 to 5 carbons in the normal chain in the case of $(CH_2)_n$, from 1 to 4 carbons in the normal chain in the case of $(CH_2)_p$ and from 1 to 6 carbons in the normal chain in the case of $(CH_2)_q$, and may contain one or more lower alkyl and/or halogen substituents. Examples of $(CH_2)_m$, $(CH_2)_n$, $(CH_2)_p$ and $(CH_2)_q$ groups include $CH_2$,

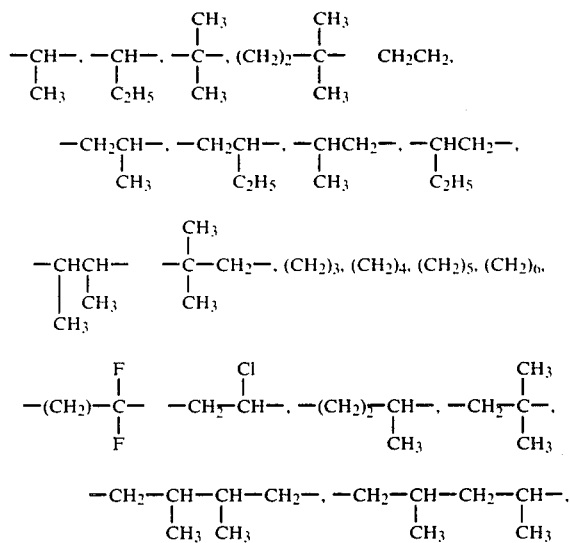

and the like.

The term "amide" refers to the group

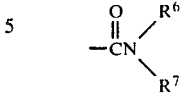

wherein $R^6$ and $R^7$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein m is 1, A is a —CH=CH—, n is 3 or 4, $R^1$ is $CO_2H$; p is 1; X is O, q is 1, $R^2$ is H, and $R^3$ is hydroxyaryl such as hydroxyphenyl or lower alkyl, such as pentyl, hexyl, or heptyl.

The compounds of formula I of the invention may be prepared as described below.

A. Where p is 1, m is 1, X is O or S (1) Starting materials where X is O

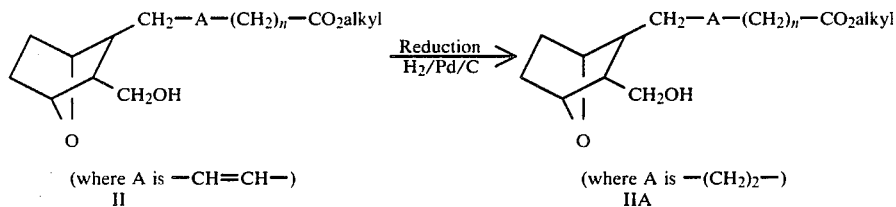

(2) Starting materials where X is S

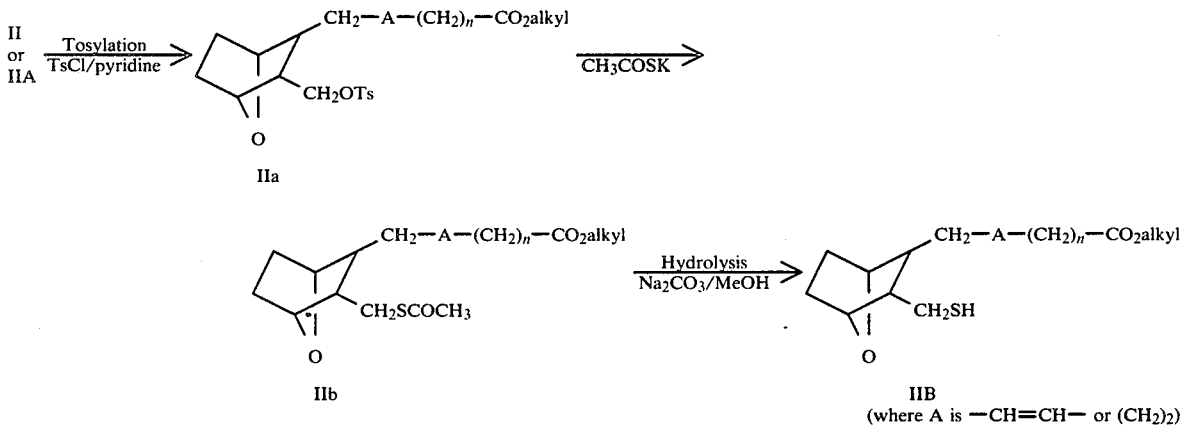

(3) Preparation of Final Products

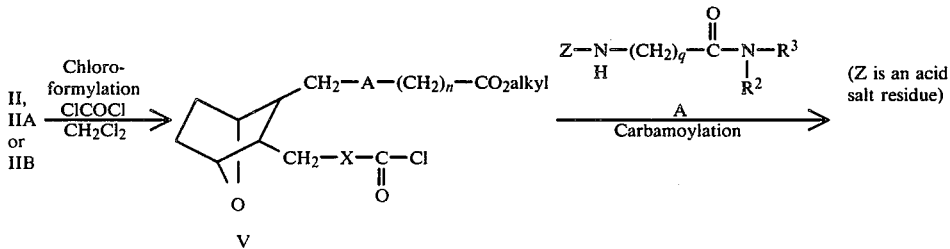

-continued
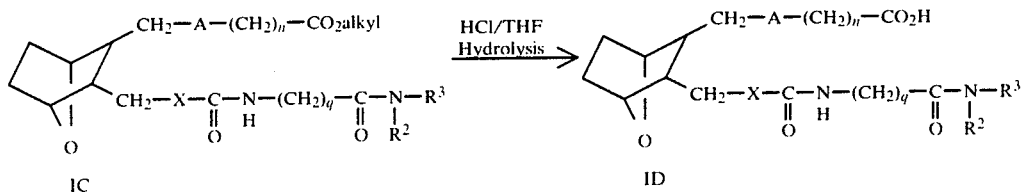
B. Where p is 2 to 5, m is 1 and X is O
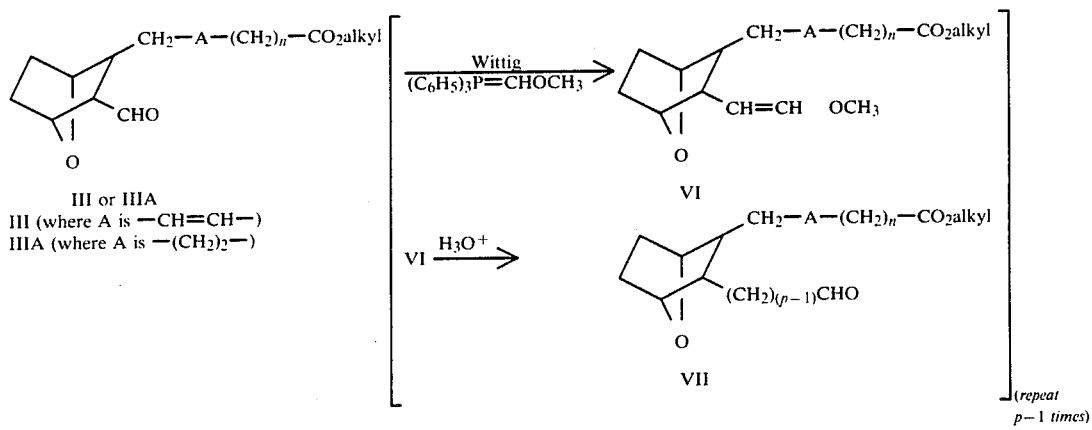
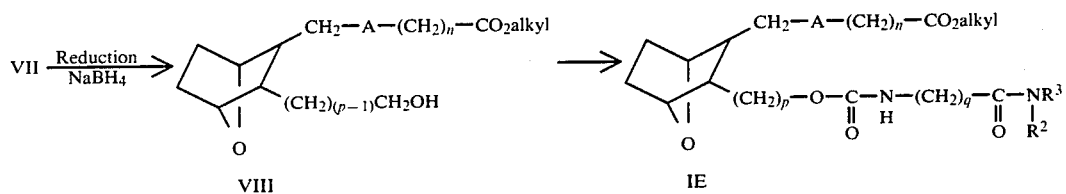
B'. Where p is 2 to 5 and X is S
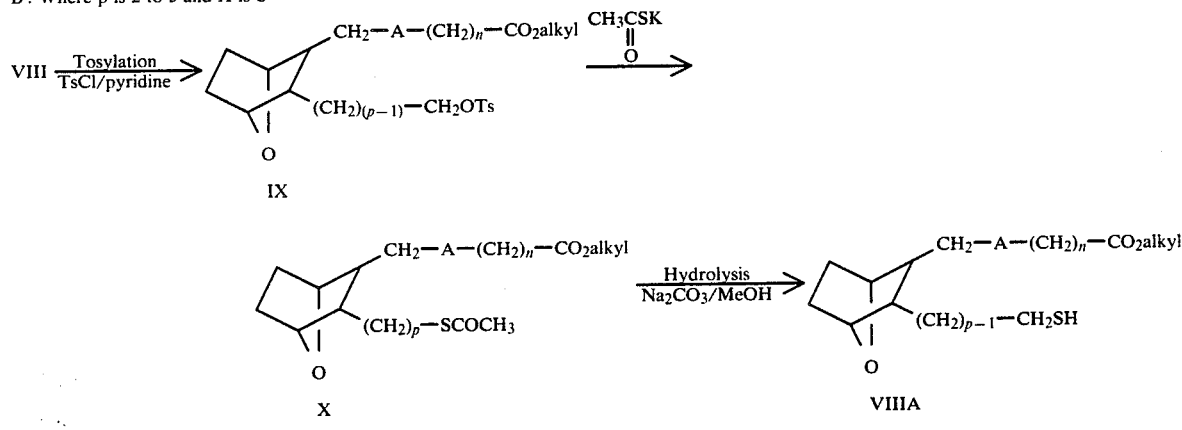
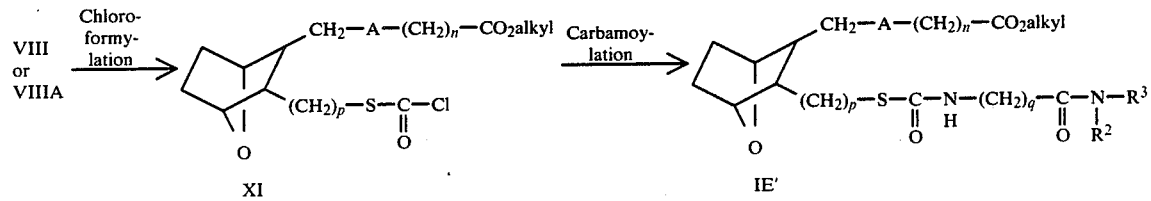
C. Where m is 2, p is 1 and X is O 4,670,453
-continued
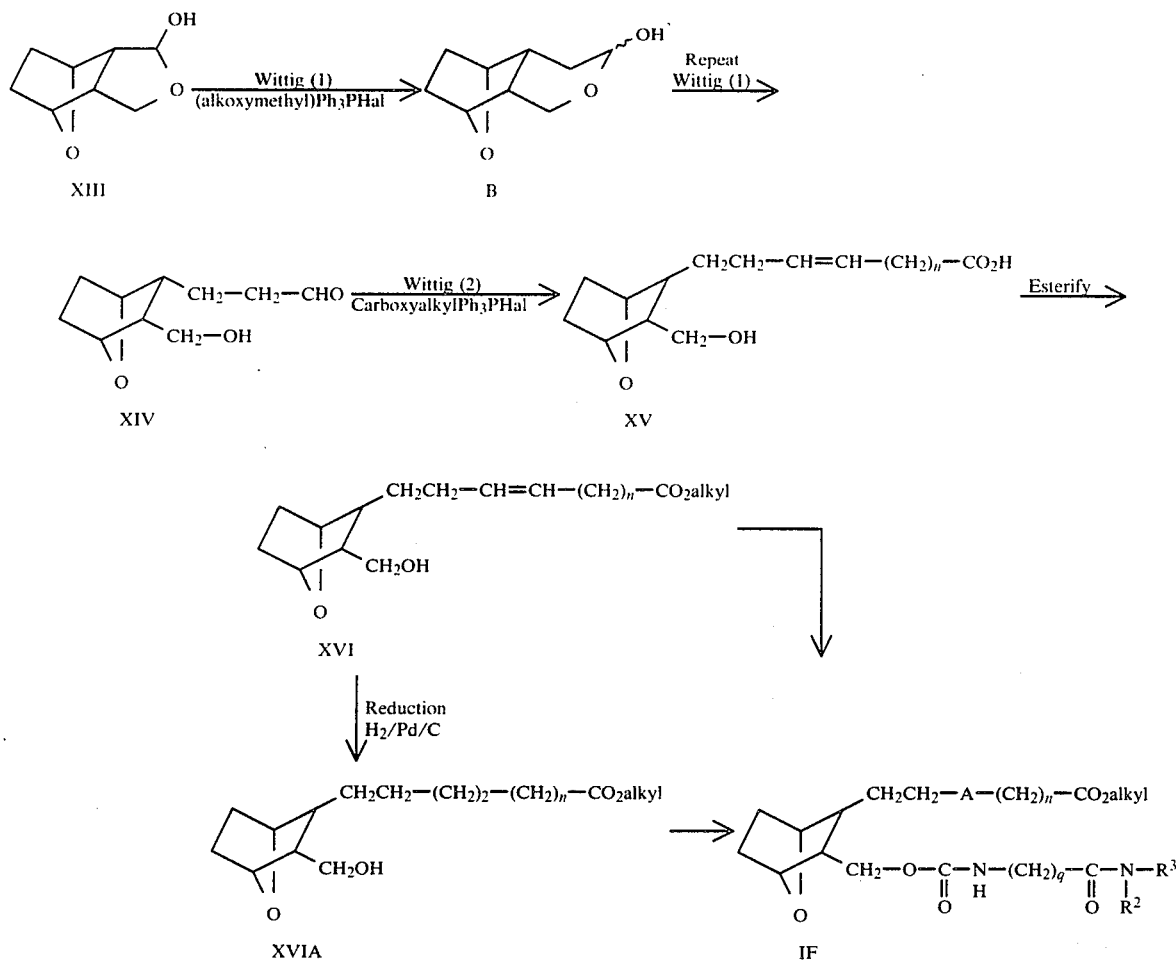
D. m is 2, p is 1 and X is S
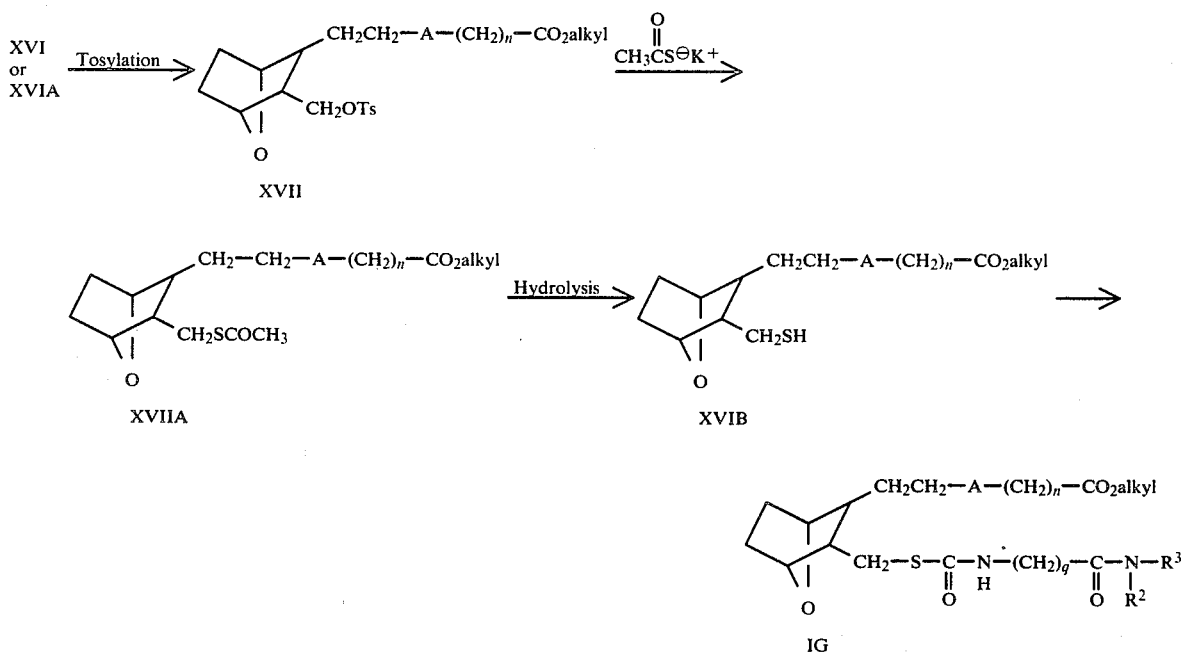
E. Where m is 3 or 4, p is 1, A is —CH═CH— and X is O

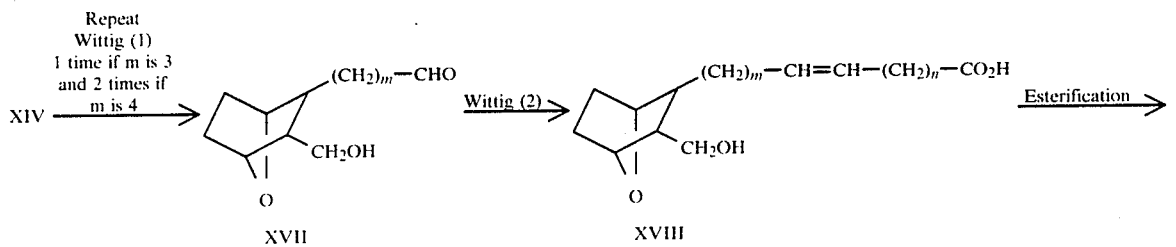
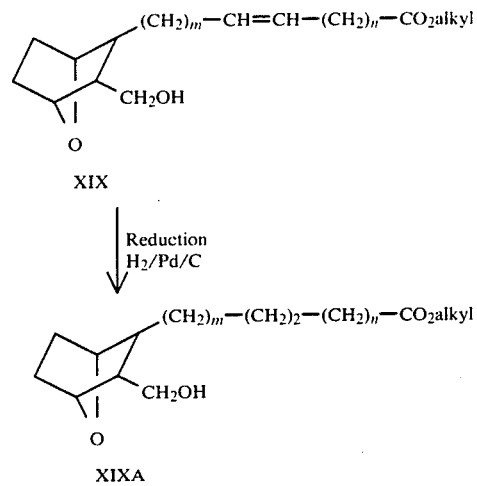
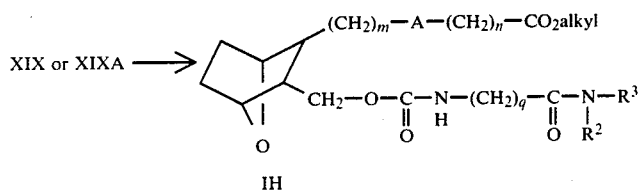
F. Where m is 3 or 4, p is 1 and X is S
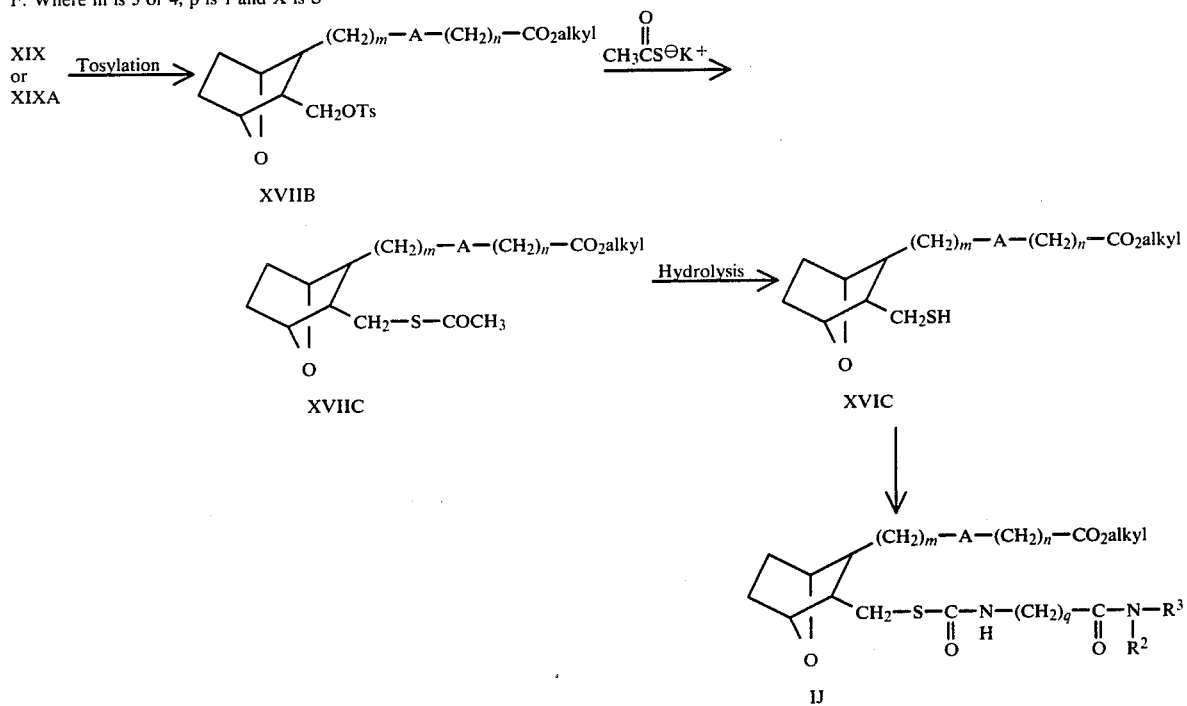
G. Where m = 0, A is —CH=CH— or (CH₂)₂, p is 1, X is O or S -continued
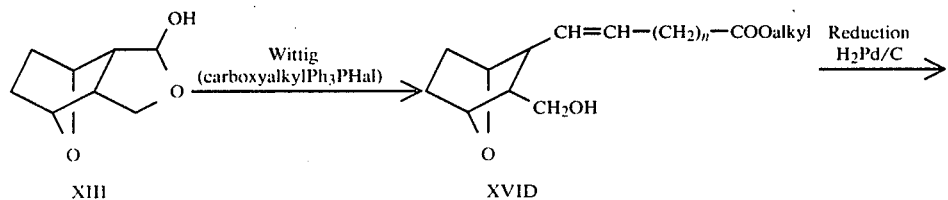
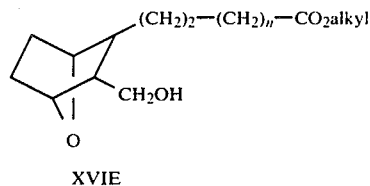
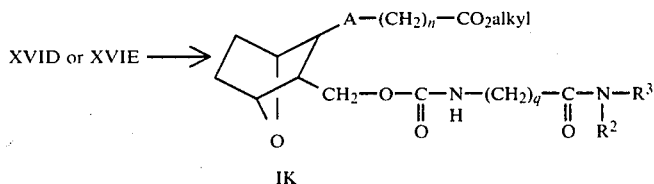
H. Where m = O, p is 1, and X is S
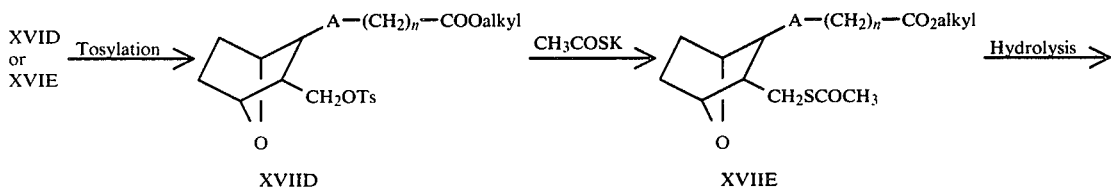
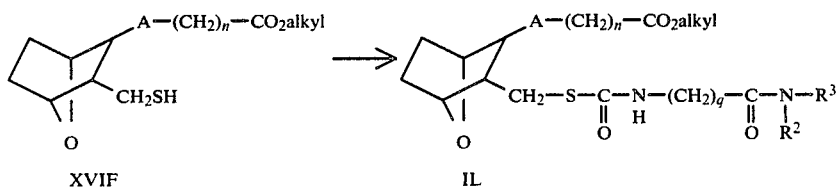
J. Where $R^1$ is $\overset{O}{\overset{\|}{C}}NR^4R^5$
IC, ID, IE, IF, IG, IH, IJ, IK or IL $\xrightarrow{HNR^4R^5}$
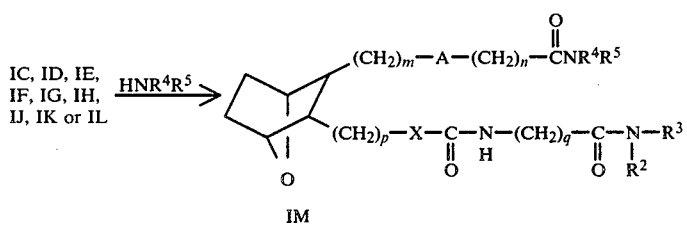
K. Where $R^1$ is $-\!\!\!<\!\!\!\begin{array}{c}N-N\\ \|\\ N-N\\ H\end{array}$ and X is O -continued
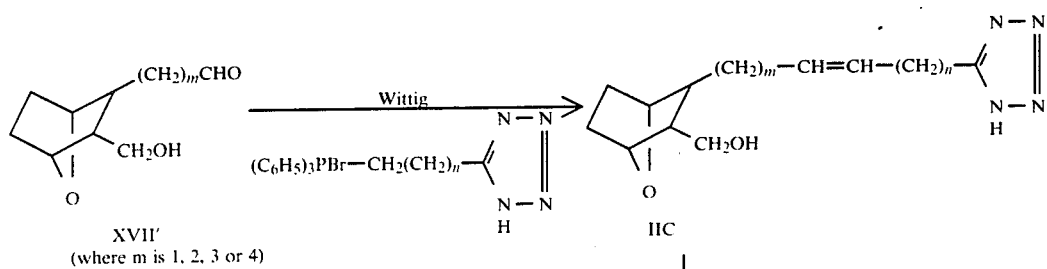
XVII'
(where m is 1, 2, 3 or 4)
IIC
Reduction
H₂Pd/C
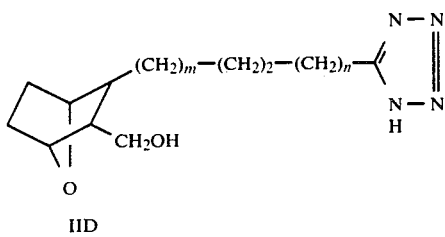
IID
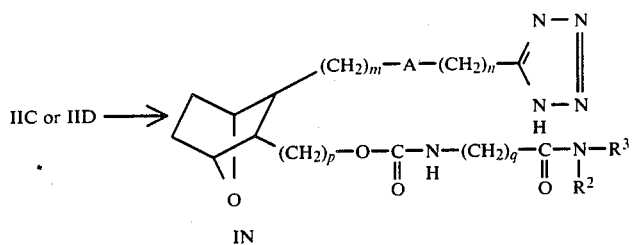
IN
L. Where $R^1$ is ─⟨tetrazole⟩ and X is S
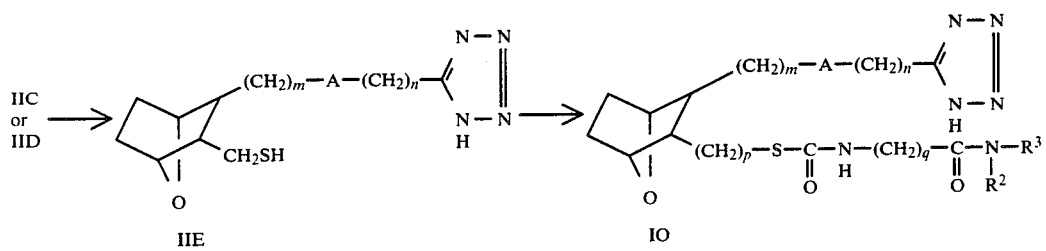
IIE
IO
M. Where $R^1$ is $\overset{O}{\underset{R^4}{\overset{\|}{C}}}N-OR^{5'}$
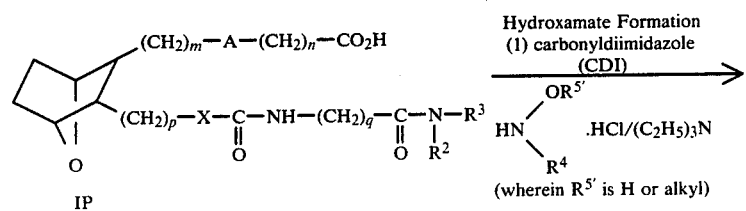
IP
Hydroxamate Formation
(1) carbonyldiimidazole
(CDI)
$\underset{R^4}{HN}-OR^{5'}$ · HCl/(C₂H₅)₃N
(wherein $R^{5'}$ is H or alkyl)

-continued

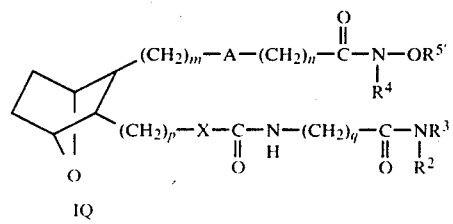

IQ

N. Where $R^1$ is $CO_2H$

IA to IL $\xrightarrow[\text{HCl}]{\text{Hydrolysis}}$

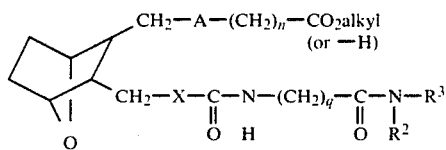

IP

As seen in reaction sequence "A", compounds of the invention where p is 1, m is 1 and $R^1$ is $CO_2$ alkyl, or $CO_2H$, that is

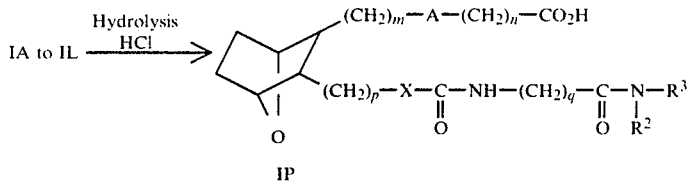

are prepared by chloroformylating the lower alkyl ester containing the hydroxymethyl group, that is, compound II or IIA, (prepared as described in U.S. Pat. No. 4,143,054) or the thiol compound IIB prepared as shown in reaction scheme A.2), by reacting II, IIA or IIB with phosgene in the presence of methylene chloride to form the corresponding acid chloride V which is subjected to a carbamoylation reaction by treating V with amine salt A

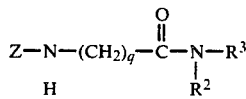

A wherein Z is an acid salt residue such as trifluoroacetic acid salt, hydrochloric acid salt, or methane sulfonic acid salt in the presence of pyridine to form the ester IC. Ester IC may then be hydrolyzed to the corresponding acid ID.

The reaction sequence identified as "B" is employed to prepare compounds of the invention wherein p is 2 to 5, m is 1, X is O, and R is $CO_2$alkyl, that is, IE,

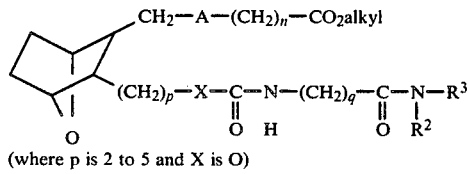

(where p is 2 to 5 and X is O)

Compound II or IIA is used to form the aldehyde III (where A is —CH═CH—) or IIIA (where A is —(CH$_2$)$_2$—). Thus, to form aldehyde III where A is —CH═CH—, compound II is subjected to a Collins oxidation, for example, by reacting II with chromium trioxide in pyridine. To form the aldehyde IIIA (where A is —(CH$_2$)$_2$—) compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$). The aldehyde III or IIIA is used to prepare aldehyde VII (where p is 2-5) by carrying out a homologation sequence, such as a Wittig reaction with (C$_6$H$_5$)$_3$P═CHOMe followed by hydrolysis, (p−1) times. The aldehyde VII (where p is 2-5) is then carried on to compounds of this invention IE where p is 2-5, that is by reducing aldehyde VII by reacting with a reducing agent such as sodium borohydride to form alcohol VIII

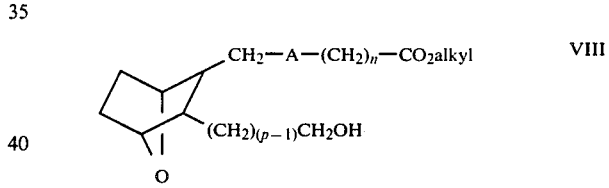

VIII

Alcohol VIII may then be converted to compound IE employing the chloroformylation and carbamoylation sequence described with respect to sequence "A".

As seen in reaction sequence "B'", compounds of the invention IE' wherein p is 2 to 5 and X is S may be prepared by converting alcohol VIII to the corresponding thiol VIIIA and then subjecting thiol VIIIA to chloroformylation and carbamoylation.

Compounds of the invention IF wherein m is 2, A is —CH═CH—, X is O and p is 1 may be prepared as outlined in reaction sequence "C" by subjecting starting compound XIII to a Wittig reaction, referred to as Wittig (1), by reacting XIII with an alkoxymethyltriphenyl phosphonium halide, such as (methoxymethyl)triphenylphosphonium chloride, for example, as described in Example 4 of U.S. Pat. No. 4,143,054, to form compound B. The Wittig (1) procedure is repeated on compound B to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II (or the reduced ester XVIA as employed in place of IIA) in reaction scheme "A" to form compound IF of the invention.

Compounds of the invention IG wherein m is 2, p is 1 and X is S may be prepared as shown in reaction scheme "D" by converting ester XVI or XVIA to the corresponding thiol XVIB which is then subjected to chloroformylation and carbamoylation to form ester IG.

Referring to reaction sequence "E", compounds of the invention wherein m is 3 or 4, A is —CH=CH—, p is 1 and X is O may be prepared by subjecting aldehyde XIV to the Wittig (1) procedure one time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II (or the reduced ester XIXA is employed in place of IIA) in reaction scheme "A" to form compound IH of the invention.

As seen in reaction sequence "F", compounds of the invention wherein m is 3 or 4, p is 1, and X is S may be prepared by converting hydroxymethyl compound XIX or XIXA to the corresponding thiol compound XVIC which is then employed in place of compound II oe IIA in reaction scheme "A" to form compound IJ of the invention.

Thus, compounds of the invention wherein m is 2, 3 or 4 and p is 2, 3 or 4 may be prepared by substituting hydroxymethyl compound XVI, XVIA, XVIB, XIX, XIXA or XVIC in place of hydroxymethyl compound II or IIA in reaction sequences A and B.

Referring now to reaction sequence "G", compounds of the invention wherein m is 0, and A is CH=CH or (CH$_2$)$_2$, p is 1, that is, compound IK may be prepared by subjecting compound XIII (prepared as described in Example 3 of U.S. Pat. No. 4,143,054) to a Wittig reaction, for example, as described in Example 6(c) of U.S. Pat. No. 4,143,054, by reacting XIII with a carboxyalkyltriphenyl phosphonium halide, such as carboxypentyltriphenyl phosphonium bromide to form the hydroxymethyl compound XVID; XVID or its reduced form XVIE may then be used to form the ester IK which, in turn, may be hydrolyzed to the corresponding acid.

As seen in reaction sequence "H", where it is desired to prepare compounds of the invention wherein m is 0, p is 1 and X is S, the hydroxymethyl compound XVID or XVIE is converted to the thiol XVIF which is then used to form ester IL which then may be hydrolyzed to the corresponding acid.

In reaction sequence "J", amides of the invention of structure IM

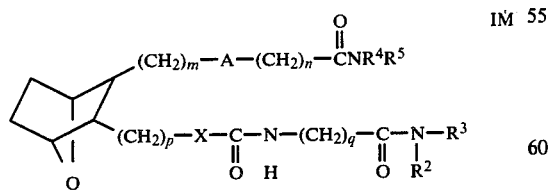

IM wherein R$^4$ and R$^5$ are independently H, alkyl or aryl are prepared by treating ester IC to IH, IJ, IK or IL with an amine of the structure E

HNR$^4$R$^5$  E.

Compounds of the invention wherein R$^1$ is tetrazole

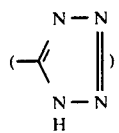

and A is CH=CH or (CH$_2$)$_2$ are prepared as described in reaction sequence "K" wherein alcohol XVII'

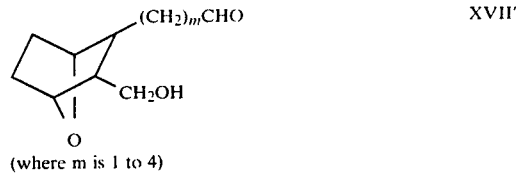

XVII'

(where m is 1 to 4)

(prepared as described in U.S. Pat. No. 4,143,054) is reacted with a Wittig reagent of the structure G

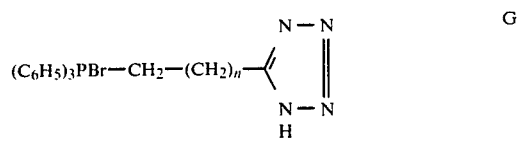

G in the presence of a base, such as potassium t-butoxide or sodium hydride-dimethyl sulfoxide employing a molar ratio of XVII':G of within the range of from about 1:1 to about 0.2:1 to form the hydroxymethyl compound IIC

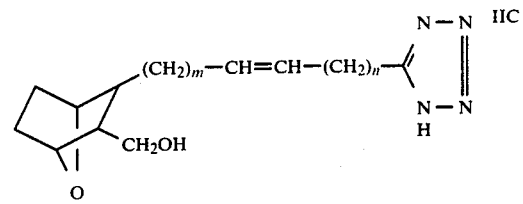

IIC which itself (or its reduced form IID) may then be employed in reaction sequences "A" and "B" in place of compounds II or IIA to form compounds of the invention IN where A is —CH=CH— or (CH$_2$)$_2$

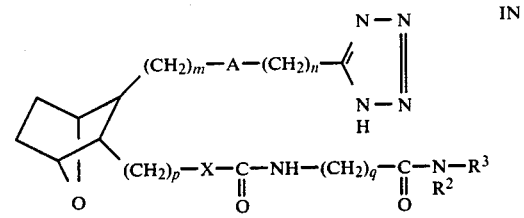

IN

Referring to reaction sequence "L", compound of the invention wherein R$^1$ is

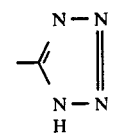

and X is S are prepared by converting compound IIC or IID to the corresponding thiol IIE, employing procedures as described in sequence A(2) and then converting thiol IIE to compound IO employing procedures described hereinbefore in sequence "A". Alternatively, compound IN or IO where A is (CH₂)₂ may be prepared by reducing compound IN or IO where A is CH=CH by treating with H₂ in the presence of palladium on charcoal.

In the reaction sequence identified as "M" where in Formula I, R¹ is

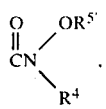

wherein R⁵' is H or alkyl, a solution of acid IP dissolved in an inert organic solvent such as tetrahydrofuran (THF) is treated with carbonyldiimidazole (CDI) and the mixture is stirred at room temperature under nitrogen. The resulting active ester is added dropwise into a cold solution of amine hydrochloride H

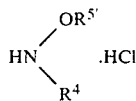   H (wherein R⁵' is H or alkyl, employing a molar ratio of active ester:H of within the range of from about 0.3:1 to about 1:1 and preferably from about 0.5:1) and triethylamine in tetrahydrofuran to form the hydroxamate IQ.

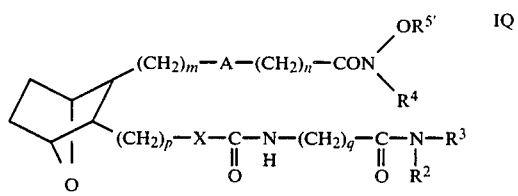   IQ

Referring to reaction sequence "N", the esters IA to IL can be converted to the free acid, that is, IP

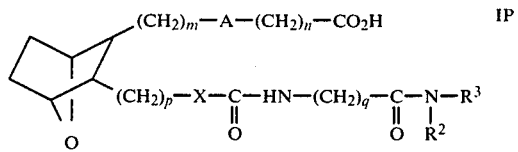   IP by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IP.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

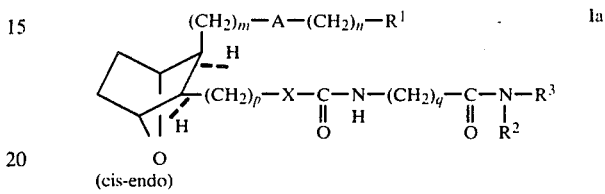   Ia
(cis-endo)

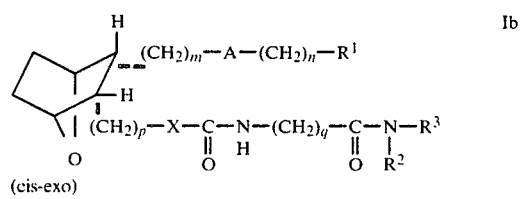   Ib
(cis-exo)

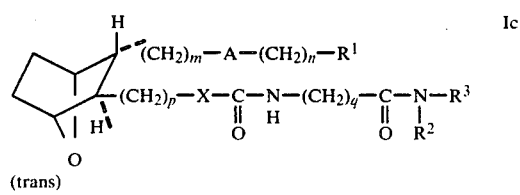   Ic
(trans)

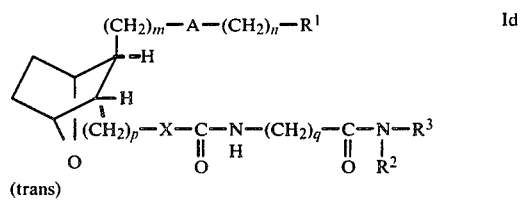   Id
(trans)

The nucleus in each of the compounds of the invention is depicted as

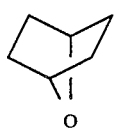

for matter of convenience; it will also be appreciated that the nucleus in the compounds of the invention may be depicted as

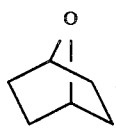

The compounds of this invetnion are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane A₂ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1β,2α(5Z),3α,4β]-7-[3-[[[[[2-[(4-Hydroxyphenyl)amino]-2-oxoethyl]amino]carbonyl]oxy]methyl]-7-oxabicyclo[2.2.1]hept-2-yl]-5-heptenoic acid

A.

[1β,2α(5Z),3α,4β]-7-[3-[(Chloroformyloxy)methyl]-7-oxabicyclo[2.2.1]hept-2-yl]-5-heptenoic acid, methyl ester and

B.

[1β,2α(5Z),3α,4β]-7-[3-[[[[2-[4-Acetoxyphenyl)amino]-2-oxoethyl]amino]carbonyl]oxy]methyl]-7-oxabicyclo[2.2.1]hept-2-yl]-5-heptenoic acid, methyl ester To a solution of 268 mg of [1β,2α(5Z),3α,4β]-7-[3-(hydroxymethyl)-7-oxabicyclo[2.2.1]hept-2-yl]-5-heptenoic acid, methyl ester (prepared as described in U.S. Pat. Nos. 4,500,723 and 4,143,054) (1 mmole) in 5 ml of dry $CH_2Cl_2$ at 0° C. under an argon atmosphere was added dropwise 6 ml of a 12.5% solution of phosgene in benzene. After stirring at 25° C. for 2 hours the excess phosgene was purged by a stream of argon to leave a solution of title A compound in $CH_2Cl_2$. To this solution at 25° C. was added 700 ml of a trifluoroacetic acid salt of 2-oxo-2-(4-acetoxyanilinyl)ethylamine (2 mmole, 2 equivalents) and 1 ml of pyridine. The stirring was continued for 1 hour at 25° C. and the reaction mixture was diluted with 30 ml of $CH_2Cl_2$. The solution was washed with 10 ml of 1N HCl, 10 ml of $H_2O$, then dried ($MgSO_4$) and concentrated. The residue was triturated with ether to yield 230 mg of title B compound as a white solid.

C.

[1β,2α(5Z),3α,4β]-7-[3-[[[[2-[(4-Hydroxyphenyl)amino]-2-oxoethyl]amino]carbonyl]oxy]methyl]-7-oxabicyclo[2.2.1]hept-2-yl]-5-heptenoic acid To a solution of 220 mg of Part B ester (0.43 mmole) in 8 ml of THF at 25° C. was added 2 ml of a 6N HCl solution. After stirring at 25° C. for 28 hours, the reaction mixture was diluted with 30 ml of $CH_2Cl_2$. The layers were separated, and the aqueous layer was extracted with two 10 ml portions of $CH_2Cl_2$. The combined organic layer was dried ($MgSO_4$) and concentrated to leave 210 mg of a white foam. This was purified on a silica gel column. Elution with 5%–10% MeOH/$CH_2Cl_2$ gave 112 mg of title product as a white foam. TLC: Silica gel,; 10% MeOH/$CH_2Cl_2$; $R_f$=0.31. $[\alpha]_D$= +7.3, C=1.5 mg/ml MeOH.

Anal calcd for $C_{23}H_{30}N_2O_7 \cdot 0.3H_2O$: C, 61.13; H, 6.83; N, 6.20. Found: C, 61.19; H, 6.87; N, 6.07.

EXAMPLE 2

[1β,2α(5Z),3α,4β]-7-[3-[[[[2-(Butylamino)-2-oxoethyl]amino]carbonyl]oxy]methyl]-7-oxabicyclo][2.2.1]hept-2-yl]-5-heptenoic acid To a solution of ca. 1 mmole of [1β,2α(5Z),3α,4β]-7-[3-(chloroformyloxymethyl)-7-oxabicyclo[2.2.1]hept-2-yl]-5-heptenoic acid, methyl ester (prepared as described in Example 1 Part A) in 10 ml of $CH_2Cl_2$ was added 490 mg of a trifluoroacetic acid salt of 2-oxo-(n-butylamino)ethylamine (2 mmole, 2 equivalents) and 1 ml of pyridine. The stirring was continued for 1 hour at 25° C. and the reaction mixture was diluted with 30 ml of $CH_2Cl_2$. The solution was washed with 10 ml of 1N HCl, 10 ml of $H_2O$, then dried ($MgSO_4$) and concentrated to give 330 mg of a crude oil. This oil was purified on a silica gel column. Elution with 50% EtOAc/hexane gave 95 mg of [1β,2α(5Z),3α,4β]-7-[3-[[[[2-(butylamino)-2-oxoethyl]amino]carbonyl]oxy]methyl]-7-oxobicyclo[2.2.1]hept-2-yl]-5-heptenoic acid, methyl ester as a clear oil.

To a solution of 95 mg of Part A ester (0.22 mmole) in 4 ml of THF at 25° C. was added 1 ml of a 6N HCl solution. After stirring at 25° C. for 20 hours, the reaction mixture was diluted with 10 ml of $CH_2Cl_2$. The layers were separated, and the aqueous layer was dried ($MgSO_4$) and concentrated to give 75 mg of crude product. Purification was done on a silica gel column. Elution with 3% MeOH/$CH_2Cl_2$ gave 28 mg of title compound as an oil. TLC: silica gel; 10% MeOH/$CH_2Cl_2$; $R_f$=0.37. $[\alpha]_D$= +2.2°, C=2.7 mg/ml MeOH.

Anal calcd for $C_{21}H_{34}N_2O_6 \cdot 0.55H_2O$: C, 60.00; H, 8.42; N, 6.66. Found: C, 60.00; H, 8.31; N, 6.29.

EXAMPLE 3

[1β,2α(5Z),3α(R),4β]-7-[3-[[[[2-[(4-Hydroxyphenyl)amino]-2-oxoethyl]amino]carbonyl]thio]methyl]-7-oxabicyclo[2.2.1]hept-2-yl]-5-heptenoic acid

A.

[1β,2α(5Z),3α,4β]-7-[3-(Mercaptomethyl)-7-oxabicyclo[2.2.1]hept-2-yl]-5-heptenoic acid, methyl ester (1)

[1β,2α(5Z),3α,4β]-7-[3-(Tosyloxymethyl)-7-oxabicyclo[2.2.1]hept-2-yl]-5-heptenoic acid, methyl ester Tosyl chloride (4.256 g, 22.4 mmol) dissolved in CH₂Cl₂ (30 ml) was added dropwise to a magnetically stirred solution of [1β,2α(5Z),3α,4β]-7-[3-(hydroxymethyl)-7-oxabicyclo[2.2.1]hept-2-yl]-5-heptenoic acid, methyl ester (prepared as described in U.S. Pat. No. 4,143,054) (3 g, 11.2 mmol) in pyridine (30 ml) at 0° C. After completion of the addition, the reaction was warmed at room temperature and stirred overnight. The reaction was poured into ice/H₂O and stirred for 30 minutes. The products were extracted with EtOAc (80 ml×3). The combined EtOAc layers were washed with 3N-HCl (40 ml×3), saturated NaHCO₃, brine and dried over MgSO₄. Filtration and evaporation of solvent gave a white solid, which was crystallized from isopropyl ether to give the corresponding title tosylate in the form of needle crystals (4.23 g, 89%), m.p. 68°–70° C.

(2)

[1β,2α(5Z),3α,4β]-7-[3-(Acetylthiomethyl)-7-oxabicyclo[2.2.1]hept-2-yl]-5-heptenoic acid, methyl ester To a solution of 1.18 g Example 3 Part A tosylate (3 mmole) in 30 ml of dry THF is added with stirring 1.14 g potassium thioacetate (10 mmole). The reaction mixture is heated under reflux for several hours, whereupon it is cooled, diluted with ethyl acetate and washed with water. The organic layer is dried over anhydrous magnesium sulfate and concentrated. The crude residue is chromatographed on a silica gel column and eluted with 5–20% ethyl acetate in hexane to give the title thioacetate.

(3)

[1β,2α(5Z),3α,4β]-7-[3-(Mercaptomethyl)-7-oxabicyclo[2.2.1]hept-2-yl]-5-heptenoic acid, methyl ester To a solution of 620 mg Part A (2) thioacetate (2 mmole) in 10 ml of methanol is added with stirring at 0°–5° C., 700 mg powdered potassium carbonate (5 mmole). The reaction mixture is stirred for a few hours at 0°–5° C. whereupon it is diluted with ethyl acetate and washed with water. The organic extract is separated and dried over anhydrous magnesium sulfate. Removal of solvent under reduced pressure gives the title thiol.

B.

[1β,2α(5Z),3α,4β]-7-[3-[(Chloroformylthio)methyl]-7-oxabicyclo[2.2.1]hept-2-yl]-5-heptenoic acid, methyl ester and

C.

[1β,2α(5Z),3α(R),4β]-7-[3-[[[[2-[4-(Acetoxyphenyl)amino]-2-oxoethyl]-amino]carbonyl]thio]methyl]-7-oxabicyclo[2.2.1]hept-2-yl]-5-heptenoic acid, methyl ester Following the procedure of Example 1 Parts A and B except substituting the Example 3 Part A ester for the [1β,2α(5Z),3α,4β]-7-[3-(hydroxymethyl)-7-oxabicyclo[2.2.1]-hept-2-yl]-5-heptenoic acid, methyl ester, the title compounds are obtained.

D.

[1β,2α(5Z),3α(R),4β]-7-[3-[[[[2-[(4-Hydroxyphenyl)amino]-2-oxoethyl]-amino]carbonyl]thio]methyl]-7-oxabicyclo[2.2.1]hept-2-yl]-5-heptenoic acid Following the procedure of Example 1 Part C except substituting the above Part C ester for the Example 1 Part B ester, the title compound is obtained.

EXAMPLE 4

[1β,2α(5Z),3α,4β]-N-Methyl-7-[[[[[-2-(Butylamino)-2-oxoethyl]amino]carbonyl]oxy]methyl]-7-oxabicyclo[2.2.1]hept-2-yl]-5-heptenamide 40% MeNH₂ in H₂O (2 ml) is added to a magnetically stirred solution of ester prepared in Example 2 (300 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 5

(1β,2α,3α,4β)-7-[3-[[[[2-(Butylamino)-2-oxoethyl]amino]carbonyl]oxy]methyl]-7-oxabicyclo[2.2.1]hept-2-yl]heptanoic acid

A.

(1β,2α,3α,4β)-7-[3-(Hydroxymethyl)-7-oxabicyclo[2.2.1]hept-2-yl]-heptanoic acid, methyl ester To 800 mg (3.0 mmole) of the [1β,2α(Z),3α,4β]-7-[3-(hydroxymethyl)-7-oxabicyclo[2.2.1]-hept-2-yl]-5-heptenoic acid, methyl ester (prepared as described in U.S. Pat. No. 4,143,054) dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

(1β,2α,3α,4β)-7-[3-[[[[2-(Butylamino)-2-oxoethyl]amino]carbonyl]oxy]methyl]-7-oxabicyclo[2.2.1]hept-2-yl]heptanoic acid Following the procedure of Examples 1 Part A and Example 2 except substituting the above Part A alcohol-ester for the alcohol ester employing in Example 1 Part A, the title product is obtained.

EXAMPLE 6

[1β,2α(5Z),3α,4β]-7-[3-[[[[2-(Butylamino)-2-oxoethyl-]amino]carbonyl]oxy]ethyl]-7-oxabicyclo[2.2.1]hept-2-yl]-5-heptenoic acid

A.

[1β,2α(Z),3α,4β]-7-[3-(2-Oxo)ethyl-7-oxabicyclo[2.2.1-]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride $((C_6H_5)_3P^+-CH_2OCH_3Cl^-)$ and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1S-[1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH4Cl, and extracted with ether (4×200 ml). The combined ether phases were washed with NaCl, saturated solution, and dried (MgSO4) and concentrated to yield a yellow oil in a white crystalline solid (phosphine oxide). The white solid was triturated with EtOAc and the mother liquor was purified by chromatography on an LPS-1 silica column. The fractions obtained were (A) [1S-[1β,2α(Z),3α,4β]]-7-[3-(2-oxo)ethyl-7-oxabicyclo[2.2.1-]hept-2-yl]-5-heptenoic acid, methyl ester, (B) [1S-[1β,2α(Z),3α,4β]]-7-[3-(2-methoxy)ethenyl-7-oxabicyclo[2.2.1]hept-2-yl]-5-heptenoic acid, methyl ester, and (C) [1S-[1β,2α(Z),3α,4β]]-7-[3-(2,2-dimethoxy)ethyl-7-oxabicyclo[2.2.1]-hept-2-yl]-5-heptenoic acid, methyl ester.

Compounds (B) and (C) are each treated with trifluoroacetic acid to convert each to compound (A).

B.

[1β,2α(5Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH4 (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO3, saturated NaCl and dried (MgSO4). The ether is evaporated to yield the title B compound.

C.

[1β,2α(Z),3α,4β]-7-[3-[[[[2-(Butylamino)-2-oxoethyl-]amino]carbonyl]oxy]ethyl]-7-oxabicyclo[2.2.1]hept-2-yl]-5-heptenoic acid Following the procedure of Example 1 Part A and Example 2 except substituting the above part B alcohol for the alcohol used in Example 1 Part A, the title compound is obtained.

EXAMPLE 7

(1β,2α,3α,4β)-7-[3-[[[[2-(Butylamino)-2-oxoethyl-]amino]carbonyl]oxy]ethyl]-7-oxabicyclo[2.2.1]hept-2-yl]-5-heptanoic acid Following the procedures of Example 5 and 2 except substituting (1β,2α,3α,4β)-7-[3-(hydroxymethyl)-7-oxabicyclo[2.2.1]hept-2-yl]heptanoic acid, methyl ester for [1β,2α(Z),3α,4β]-7-[3-(hydroxymethyl)-7-oxabicyclo[2.2.1]hept-2-yl]-5-heptenoic acid, methyl ester, the title compound is obtained.

EXAMPLE 8

[1β,2α(5Z),3α,4β]-7-[3-[4-[[[[2-(Butylamino)-2-oxoethyl]amino]carbonyl]oxy]butyl]-7-oxabicyclo[2.2.1-]hept-2-yl]-5-heptenoic acid

A.

[1β,2α(5Z),3α,4β]-7-[3-(3-Oxo)propyl-7-oxabicyclo[2.2.1]hept-2-yl]-5-heptenoic acid, methyl ester Following the procedure of Example 6 Part A except substituting [1β,2α(Z),3α,4β]-7-[3-(2-oxo)-ethyl-7-oxabicyclo[2.2.1]hept-2-yl]-5-heptenoic acid, methyl ester for [1β,2α(Z),3α,4β]-7-[3-formyl-7-oxabicyclo[2.2.1]hept-2-yl]-5-heptenoic acid, methyl ester, the title A compound is obtained.

B.

[1β,2α(Z),3α,4β]-7-[3-(4-Oxo)butyl-7-oxabicyclo[2.2.1-]hept-2-yl]5-heptenoic acid, methyl ester Following the procedure of Example 6 Part A except substituting the aldehyde from Part A above for [1β,2α(Z),3α,4β]-7-[3-formyl-7-oxabicyclo[2.2.1]hept-2-yl]-5-heptenoic acid, methyl ester, the title B compound is obtained.

C.

[1β,2α(Z),3α,4β]-7-[3-(4-Hydroxybutyl)-7-oxabicyclo[2.2.1]hept-2-yl]-5-heptenoic acid, methyl ester Following the procedure of Example 6 Part B except substituting the title B aldehyde for [1β,2α(Z),3α,4β]-7-[3-(2-oxo)ethyl-7-oxabicyclo[2.2.1]hept-2-yl]-5-heptenoic acid, methyl ester, the title C alcohol is obtained.

D.

[1β,2α(Z),3α,4β]-7-[3-[4-[[[[2-(Butylamino)-2-oxoethyl-]amino]carbonyl]oxy]butyl]-7-oxabicyclo[2.2.1]hept-2-yl]-5-heptenoic acid Following the procedure of Example 1 Part A and Example 2 except substituting the above Part C alcohol for the alcohol used in Example 1 Part A, the title compound is obtained.

EXAMPLE 9

[1β,2α(5Z),3α,4β]-8-[3-[[[[2-(Butylamino)-2-oxoethyl-]amino]carbonyl]oxy]methyl]-7-oxabicyclo[2.2.1]hept-2-yl]-5-octenoic acid

A.

(1β,2α,3α,4β)-3-[3-(Hydroxymethyl)-7-oxabicyclo[2.2.1]hept-2-yl]propionaldehyde

A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (XIII in reaction sequence C) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO4 and concentrated in vacuo. The solid residue was triturated with hexane (1 liter), filtered, and dried in vacuo to yield 220 g (100%) of desired compound (hemiacetal B in reaction sequence C), m.p. 104°–105° C., [α]$_D$ = +27° c = 1 MeOH.

TLC: Silica gel; EtOAc; R$_f$ = 0.3; Ce(SO4)2.

The above Wittig procedure was repeated on the hemiacetal B used in place of hemiacetal XIII to form the title aldehyde.

B.

[1β,2α(Z),3α,4β]-8-[3-(Hydroxymethyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.02 g (6 mmole) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane (CH2N2) in Et2O to give the title compound.

C.

[1β,2α(Z),3α,4β]-8-[3-[[[[2-(Butylamino)-2-oxoethyl]amino]carbonyl]oxy]methyl]-7-oxabicyclo[2.2.1]hept-2-yl]-5-octenoic acid Following the procedure of Example 1, Part A, and Example 2 except substituting the title B ester for the ester used in Example 1 Part A, the title compound is obtained.

EXAMPLE 10

[1β,2α(Z),3α,4β]-6-[3-[[[[2-(Butylamino)-2-oxoethyl]amino]carbonyl]oxy]methyl]-7-oxabicyclo[2.2.1]hept-2-yl]-1-(1H-tetrazol-5-yl)-4-hexane

A.

[1β,2α(Z),3α,4β]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO3 solution, washed with 100 ml of ether, acidified with dilute HCl to pH 3, and extracted with three 500 portions of ethyl acetate. The combined organic solutions are dried over anhydrous MgSO4, and purified by silica chromatography using a 5% methanol in methylene chloride eluant to provide 2 g of title A compound.

B.

[1β,2α(5Z),3α,4β-6-[3-[[[[2-(Butylamino)-2-oxoethyl]amino]carbonyl]oxy]methyl]-7-oxabicyclo[2.2.1]hept-2-yl]-1-(1H-tetrazol-5-yl)-4-hexene Following the procedure of Example 1, Part A, and Example 2 except substituting the Part A compound for the hydroxymethyl compound used in Example 1 Part A, the title compound is obtained.

EXAMPLE 11

[1β,2α(5Z),3α,4β]-7-[3-[[[[2-(Butylamino)-2-oxoethyl]amino]carbonyl]oxy]methyl]-7-oxabicyclo[2.2.1]hept-2-yl]-N-hydroxy-N-methyl-5-heptenamide A solution of Example 2 acid (0.82 mmole) in dry tetrahydrofuran (5.0 ml) is treated with carbonyldiimidazole (CDI) (0.82 mmole) at 0° C. and stirred at 0° for 1 hour and at room temperature for 1 hour. The reaction is added dropwise into a cold solution (0°, ice-water) of 98% methylhydroxylamine hydrochloride (139.8 mg; 1.64 mmole; 2 eq.) and triethylamine (0.34 ml; 2.46 mmole; 3 eq.) in tetrahydrofuran (2ml). The mixture is stirred at 0° under nitrogen for 30 minutes and at room temperature overnight, diluted with water (10 ml) and extracted twice with dichloromethane (50 ml). The organic extract is washed with 1N HCl (10 ml), 5% NaHCO₃ (5 ml) and water (10 ml), dried (anhydrous MgSO₄), filtered and evaporated to dryness giving the crude product, which is purified by silica gel column to afford the title compound.

EXAMPLE 12

[1β,2α(6Z),3α,4β]-7-[3-[[[[2-(Butylamino)-2-oxoethyl]amino]carbonyl]oxy]methyl]-7-oxabicyclo[2.2.1]hept-2-yl]-6-heptenoic acid

A.

[1β,2α(6Z),3α,4β]-7-[3-(Hydroxymethyl)-7-oxabicyclo[2.2.1]hept-2-yl]-heptenoic acid, methyl ester A slurry of carboxypentyl triphenylphosphonium bromide in THF is cooled in an ice bath and treated dropwise with 1.4M KOt-amylate in toluene. After completion of this addition, the reaction mixture is allowed to warm to room temperature and is stirred for 6 hours. To this stirred solution is then added a solution of hemiacetal XIII (reaction sequence G) (prepared as described in Example 3 of U.S. Pat. No. 4,143,054) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated NaHCO₃ solution. The aqueous extracts are acidified to pH~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title ester.

B.

[1β,2α(6Z),3α,4β]-7-[3-[[[[2-(Butylamino)-2-oxoethyl]amino]carbonyl]oxy]methyl]-7-oxabicyclo[2.2.1]hept-2yl]-6-heptenoic acid Following the procedure of Example 1, Part A, and Example 2 except substituting the Part A ester for the hydroxymethyl compound used in Example 1 Part A, the title compound is obtained.

EXAMPLE 13

[1β,2α(2E), 3α,4β]-7-[3-[[[[2-(Butylamino)-2-oxoethyl]amino]carbonyl]oxy]methyl]-7-oxabicyclo[2.2.1]hept-2-yl]2-heptenoic acid

A.

(1β,2α,3α,4β)-5-[3-(Hydroxymethyl)-7-oxabicyclo[2.2.1]hept-2-yl]pentanal

Following the procedure of Example 9 Part A, except substituting (1β,2α,3α,4β)-3-[3-(hydroxymethyl)-7-oxabicyclo[2.2.1]hept-2-yl]propionaldehyde for the hemiacetal XIII (see reaction sequence C), (1β,2α,3α,4β)-4-[3-(hydroxymethyl)-7-oxabicyclo[2.2.1]hept-2-yl]butanal is obtained. Then by repeating the procedure of Example 9 Part A on (1β,2α, 3α,4β)-4-[3-(hydroxymethyl)-7-oxabicyclo[2.2.1]hept-2-yl]butanal, the title A aldehyde is produced.

B.

[1β,2α(2E),3α,4β]-7-[3-(Hydroxymethyl)-7-oxabicyclo[2.2.1]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C.

[1β,2α(2E),3α,4β]-7-[3-[[[[2-(Butylamino)-2-oxoethyl]amino]carbonyl]oxy]methyl]-7-oxabicyclo[2.2.1]hept-2-yl]-2-heptenoic acid Following the procedure of Example 1, Part A, and Example 2 except substituting the Part B ester for the ester used in Example 1 Part A, the title compound is obtained.

EXAMPLES 14 TO 44

Following the procedures outlined in the specification and described in the above working Examples, the following compounds may be prepared.

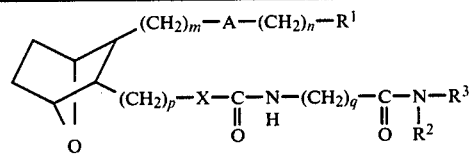

| Ex. No. | m | A | (CH₂)ₙ | X | R¹ | p | R² | R³ | (CH₂)_q |
|---|---|---|---|---|---|---|---|---|---|
| 14. | 2 | CH=CH | CH₂ | O | CO₂H | 1 | H | H | CH₂ |
| 15. | 3 | (CH₂)₂ | (CH₂)₂ | S | CO₂H | 2 | C₂H₅ | CH₃ | CH₂ |
| 16. | 4 | CH=CH | (CH₂)₃ | O | 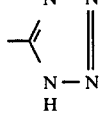 | 3 | CH₃ | —CH₂CH=CH—CH₃ | (CH₂)₂ |

-continued

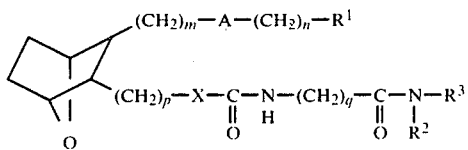

| Ex. No. | m | A | $(CH_2)_n$ | X | $R^1$ | p | $R^2$ | $R^3$ | $(CH_2)_q$ |
|---|---|---|---|---|---|---|---|---|---|
| 17. | 1 | $(CH_2)_2$ | $(CH_2)_4$ | S | $\overset{O}{\underset{\|}{C}}N(CH_3)C_2H_5$ | 1 | $CH_3$ | cyclohexyl | $(CH_3)_2$ |
| 18. | 0 | CH=CH | $(CH_2)_5$ | S | $\overset{O}{\underset{\|}{C}}\underset{CH_3}{N}-OH$ | 2 | H | $-CH_2-$cyclopentyl | $(CH_2)_3$ |
| 19. | 2 | CH=CH | $-\underset{CH_3}{\overset{\|}{CH}}-$ | O | $\overset{O}{\underset{\|}{C}}\underset{H}{N}-OCH_3$ | 3 | $C_2H_5$ | $-CH_2-\overset{H}{C}=\overset{H}{C}-CH_3$ | $(CH_2)_3$ |
| 20. | 3 | $(CH_2)_2$ | $-\underset{CH_3}{\overset{CH_3}{\overset{\|}{C}}}-$ | O | $\overset{O}{\underset{\|}{C}}\underset{CH_3}{N}-OC_2H_5$ | 4 | H | $C_6H_5$ | $(CH_2)_4$ |
| 21. | 4 | $(CH_2)_2$ | $(CH_2)_4$ | S | $\overset{O}{\underset{\|}{C}}NHC_6H_5$ | 1 | $C_3H_7$ | $C_6H_5$ | $(CH_2)_4$ |
| 22. | 1 | CH=CH | $-\underset{\|}{\overset{CH_3}{C}}\underset{}{\overset{CH_3}{\|}}-CH_2-$ | S | $CO_2Li$ | 2 | H | $CH_2C_6H_5$ | $(CH_2)_5$ |
| 23. | 0 | CH=CH | $-\underset{CH_3}{\overset{\|}{CH}}-\underset{CH_3}{\overset{\|}{CH}}-$ | O | $CO_2Na$ | 3 | $CH_3$ | $-(CH_2)_2C_6H_5$ | $(CH_2)_5$ |
| 24. | 1 | $(CH_2)_2$ | $-\underset{F}{\overset{CH_3}{\overset{\|}{C}}}-CH_2-$ | O | $CO_2$ glucamine salt | 4 | $C_2H_5$ | $-C_6H_4-p-CH_3$ | $(CH_2)_6$ |
| 25. | 2 | CH=CH | $-\underset{F}{\overset{\|}{CH}}-\underset{F}{\overset{\|}{CH}}-$ | S | $CO_2$ tris salt | 1 | H | $-C_6H_4-p-OH$ | $(CH_2)_6$ |
| 26. | 3 | $(CH_2)_2$ | $-\underset{F}{\overset{F}{\overset{\|}{C}}}-CH_2-$ | S | $CO_2H$ | 2 | $C_4H_9$ | cyclopentyl | $-\overset{CH_3}{\underset{\|}{CH}}-$ |
| 27. | 4 | $(CH_2)_2$ | $-(CH_2)_5-$ | O | tetrazolyl | 3 | H | $-CH_2-$cyclobutyl | $-CH_2-\overset{CH_3}{\underset{\|}{CH}}-$ |
| 28. | 0 | CH=CH | $-CH_2-\overset{CH_3}{\underset{\|}{CH}}-CH_2-$ | S | $\overset{O}{\underset{\|}{C}}NH_2$ | 4 | $CH_2$ | $-CH_2-$cyclohexyl | $-CH_2-\overset{CH_3}{\underset{\|}{CH}}-CH_2-$ |
| 29. | 0 | $(CH_2)_2$ | $-CH_2-\overset{CH_3}{\underset{CH_3}{\overset{\|}{C}}}-$ | S | $\overset{O}{\underset{\|}{C}}NOH$ | 1 | $C_2H_5$ | $C_6H_5$ | $CH_2-CH_2-\overset{CH_3}{\underset{CH_3}{\overset{\|}{C}}}-$ |

-continued

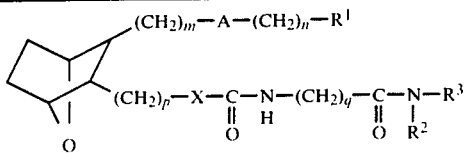

| Ex. No. | m | A | $(CH_2)_n$ | X | $R^1$ | p | $R^2$ | $R^3$ | $(CH_2)_q$ |
|---|---|---|---|---|---|---|---|---|---|
| 30. | 1 | CH=CH | $CH_2$ | O | $\underset{CN(CH_3)_2}{\overset{O}{\parallel}}$ | 2 | $H_5$ | $(CH_2)_2C_6H_5$ | $-CH_2-\underset{CH_3}{\overset{CH_3}{\underset{\vert}{\overset{\vert}{C}}}}-$ |
| 31. | 2 | $(CH_2)_2$ | $(CH_2)_2$ | S | $\underset{\underset{OH}{\vert}}{\overset{O}{\overset{\parallel}{C}}}N-CH_3$ | 3 | $CH_3$ | cyclohexyl | $-\overset{CH_3}{\underset{\vert}{CH}}-\overset{CH_3}{\underset{\vert}{CH}}-$ |
| 32. | 3 | CH=CH | $(CH_2)_3$ | O | $CO_2H$ | 4 | $C_2H_5$ | $C_6H_5$ | $-CH_2-$ |
| 33. | 4 | $(CH_2)_2$ | $(CH_2)_4$ | S | $CO_2H$ | 1 | $C_3H_7$ | $C_7H_{15}$ | $-(CH_2)_2-$ |
| 34. | 0 | CH=CH | $-CH_2\underset{F}{\overset{F}{C}}-$ | O | tetrazolyl | 2 | $C_4H_9$ | H | $-(CH_2)_3-$ |
| 35. | 1 | $(CH_2)_2$ | $-CH_2-\underset{CH_3}{\overset{CH_3}{C}}-$ | S | $\underset{CN(C_2H_5)_2}{\overset{O}{\parallel}}$ | 3 | $C_5H_{11}$ | $C_4H_9$ | $-\overset{CH_3}{\underset{\vert}{CH}}-CH_2-CH_2-$ |
| 36. | 2 | CH=CH | $(CH_2)_5$ | O | $\underset{CNHC_6H_5}{\overset{O}{\parallel}}$ | 4 | H | $-(CH_2)_2CH=CHCH_3$ | $-\overset{CH_3}{\underset{\vert}{CH}}-\underset{CH_3}{\overset{CH_3}{\underset{\vert}{C}}}-$ |
| 37. | 3 | $(CH_2)_2$ | $-\overset{CH_3}{\underset{\vert}{CH}}-\overset{F}{\underset{\vert}{CH}}-$ | S | COOH | 1 | H | $C_6H_5$ | $-(CH_2)_3-$ |
| 38. | 4 | $(CH_2)_2$ | $(CH_2)_2$ | O | tetrazolyl | 2 | H | $-CH_2C_6H_5$ | $-(CH_2)_2-$ |
| 39. | 0 | CH=CH | $(CH_2)_3$ | S | $CO_2CH_3$ | 3 | $CH_3$ | $C_4H_9$ | $-CH_2-$ |
| 40. | 2 | $(CH_2)_2$ | $(CH_2)_4$ | O | $CO_2CH_3$ | 4 | $CH_3$ | $C_6H_5$ | $-CH_2-\underset{CH_3}{\overset{CH_3}{\underset{\vert}{C}}}-$ |
| 41. | 3 | CH=CH | $(CH_2)_5$ | S | $CO_2H$ | 1 | $CH_3$ | $CH_2C_6H_5$ | $-(CH_2)_2-$ |

What is claimed is:

1. A compound having the structure

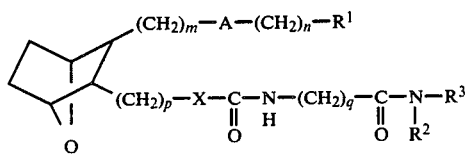

including all stereoisomers thereof, wherein m is 0 to 4; A is —CH=CH— or —CH₂—CH₂—; n is 1 to 5; $R^1$ is $CO_2H$, $CO_2$alkyl, $CO_2$ alkali metal, $CO_2$-polyhydroxyamine salt,

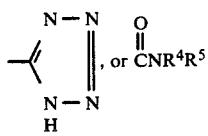, or $\overset{O}{\overset{\parallel}{C}}NR^4R^5$ wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; X is O or S; q is 1 to 6; $R^2$ is H or lower alkyl; and $R^3$ is lower alkyl, lower alkenyl containing 2 to 12 carbons, aryl, arylalkyl, cycloalkyl or cycloalkylalkyl;

$(CH_2)_m$, $(CH_2)_n$, $(CH_2)_p$ and $(CH_2)_q$ may be unsubstituted or substituted with 1 or 2 lower alkyl groups and/or 1 or 2 halogens;

wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl, alkylcycloalkyl, hydroxy, amino, amido, alkylamino, arylamino, alkanoylamino, arylcarbonylamino, thioamido, nitro, cyano, thiol, arylthio or alkylthio;

aryl alone or as part of another group contains 6 to 10 carbons in the ring portion and is unsubstituted or is substituted with 1 or 2 lower alkyl groups, 1 or 2 halogens, 1 or 2 alkoxy groups, 1 or 2 hydroxy groups, 1 or 2 amino groups, 1 or 2 alkylamino groups, 1 or 2 arylamino groups, 1 or 2 alkanoylamino groups, 1 or 2 arylcarbonylamino groups, 1 or 2 amido groups, 1 or 2 nitro groups, 1 or 2 cyano groups, 1 or 2 thioamido groups, 1 or 2 thiol groups, 1 or 2 arylthio groups and/or 1 or 2 alkylthio groups;

cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups; and alkanoyl refers to lower alkyl linked to a carbonyl group.

2. The compound as defined in claim 1 wherein $R^2$ is H and $R^3$ is alkyl or aryl.

3. The compound as defined in claim 1 wherein A is CH=CH.

4. The compound as defined in claim 1 wherein m is 1 and n is 1 to 4.

5. The compound as defined in claim 1 wherein p is 1.

6. The compound as defined in claim 1 wherein X is O.

7. The compound as defined in claim 1 wherein $R^1$ is $CO_2$ alkyl or $CO_2H$.

8. The compound as defined in claim 1 wherein m is 1, n is 2 to 4, A is CH=CH, $R^1$ is $CO_2$alkyl or $CO_2H$, p is 1, $R^2$ is H, $R^3$ is alkyl, phenyl or substituted phenyl, and X is O.

9. The compound as defined in claim 1 having the name [1β,2α(5Z),3α(R),4β]-7-[3-[[[[2-[(4-hydroxyphenyl)amino]-2-oxoethyl]-amino]-carbonyl]oxy]methyl]-7-oxabicyclo[2.2.1]hept-2-yl]-5-heptenoic acid or esters thereof, including all stereoisomers thereof.

10. The compound as defined in claim 1 having the name [1β,2α(5Z),3α(R),4β]-7-[3-[[[[2-(butylamino)-2-oxoethyl]amino]carbonyl]oxy]methyl]-7-oxabicyclo[2.2.1]hept-2-yl]-5-heptenoic acid or esters thereof, including all stereoisomers thereof.

11. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation which comprises administering to a mammalian host an effective amount of a compound as defined in claim 1 or a pharmaceutically acceptable salt thereof.

15. A method of inhibiting bronchoconstriction associated with asthma, which comprises administering to a mammalian host an effective amount of a compound as defined in claim 1 or a pharmaceutically acceptable salt thereof.

16. A method of treating peripheral vascular diseases, which comprises topically or systemically administering to a mammalian host an effective amount of a compound as defined in claim 1 or a pharmaceutically acceptable salt thereof.

* * * * *